US006451542B1

(12) United States Patent
Lee et al.

(10) Patent No.: US 6,451,542 B1
(45) Date of Patent: Sep. 17, 2002

(54) METHODS AND SYSTEMS FOR DIAGNOSING KAWASAKI DISEASE

(75) Inventors: Wen-Chuan Lee, Hsinchu; Teh-Yang Huang, Kaohsiung; Kao-Pin Hwang, Miaoli Hsien; Huey-Ching Chen; Yueh-Tsu King, both of Kaohsiung; Shyh-Shin Chiou, Taipei Hsien; Rei-Cheng Yang, Kaohsiung, all of (TW)

(73) Assignee: Animal Technology Institute Taiwan, Miaoli (TW)

( * ) Notice: Subject to any disclaimer, the term of this patent is extended or adjusted under 35 U.S.C. 154(b) by 0 days.

(21) Appl. No.: 09/371,035

(22) Filed: Aug. 10, 1999

(51) Int. Cl.$^7$ ............... G01N 33/53; C07K 14/775; C07K 14/795
(52) U.S. Cl. .......... 435/7.1; 436/71; 436/501; 530/359; 530/392
(58) Field of Search ............. 436/71, 501; 530/359, 530/392; 435/7.1

(56) References Cited

U.S. PATENT DOCUMENTS

| 5,075,236 A | 12/1991 | Yone et al. ............. 436/518 |
| 5,286,623 A | 2/1994 | Leung et al. ............ 435/6 |
| 5,470,716 A | 11/1995 | Leung et al. ............ 435/34 |

FOREIGN PATENT DOCUMENTS

WO        98/37419    *  8/1998

OTHER PUBLICATIONS

Hideaki et al., "Changes in apolipoproteins during the acute phase of Kawasaki disease", Acta Paediatrica Japonica (1995) vol. 37 pp. 672–676.*

K. Boven, E.R. DeGraeff–Meeder, W. Spliet, and W. Knis: Atypical Kawasaki Disease: an often missed diagnosis, European Journal of Pediatrics (1992) 115:577–580, pp. 321.

Wanda Dobryszycka, Biological Functions of Haptoglobin New Pieces to an Old Puzzle, European Journal Clin. Chem. Clin. Biochem (1977) 35(9): 647–654 (1997).

Michel R. Langlois and Joris R. Delanghe, Biological and clinical significance of haptoglobin polymorphism in humans, Clinical Chemistry 43:10, 1589–1600 (1996).

Wen–Chuan Lee, Kao–Pin Hwang, Hey–Ching Chen, Yueh–Tsu King, Shyh–Shin Chiou, Rei–Cheng Yang, The–Yang Huang: Formation of Coronary Artery in Kawasaki Disease Is Associated with Haptoglobin Polymorphism, Abstracts for the Sixth International Kawasaki Disease Symposium, Feb. 11–14, 1999.

* cited by examiner

*Primary Examiner*—John S. Brusca
*Assistant Examiner*—Marjorie A. Moran
(74) *Attorney, Agent, or Firm*—Kenyon & Kenyon

(57) ABSTRACT

The invention provides a method for diagnosing Kawaski Disease (KD) in a patient suspected of suffering from KD by using as an index a ratio of the level (by weight/volume, w/v) of haptoglobin (Hp) to the level (by weight/volume, w/v) of apolipoprotein A1 (Apo A1) in a patient. A system for use with the method is also included. In addition, the invention also provides a method for diagnosing Atypical Kawasaki Disease (AKD) in a patient suspected of suffering from KD by identifying the phenotype of haptoglobin in said patient and correlating the presence of Hp2-1 or Hp1-1 haptoglobin phenotype with AKD and providing immediate treatment of the patient.

10 Claims, 2 Drawing Sheets

METHODS AND SYSTEMS FOR DIAGNOSING KAWASAKI DISEASE

BACKGROUND OF THE INVENTION

1. Field of the Invention

The present invention relates to t Kawasaki Disease, including typical Kawasaki Disease and a typical Kawasaki Disease. More particular, the invention relates to methods and systems for the diagnosis of Kawasaki Disease.

2. Description of the Prior Art

Kawasaki Disease ("KD" hereafter) is first described by Tomisaku Kawasaki in 1967 in Japan. KD is an acute systemic vasculitis particularly occurring in childhood under the age of 5. The disease is characterized by prolonged fever, reddening and indurative edema of hands and feet and multiple clinical and biochemical features of inflammation and most common complications of coronary artery abnormality ("CAA" hereafter). KD has been recognized worldwide in children of all racial backgrounds. Over 125,000 cases have been reported through the end of 1994 (Shulman et al., Kawasaki Disease, Pediatric Rheumatology, 42:1205–1222, 1995); the annual incidence in Japan is 67 per 100,000 children under the age of 5; in Taiwan, this number is estimated to be 32 per 100,000 children under the age of 5. In the United States, emerging cases range from 3,000 to 5,000 annually. The disease is most commonly manifests as acute coronary artery lesions. If left untreated, serious complications and death may result.

Currently, a specific test for the diagnosis of KD does not exist. It is very difficult to diagnose KD definitely in an early stage because its etiology remains unclear. Based on the epidemiologic and clinical features of KD, it is suggested that KD may be caused by an infectious agent which has not been identified, but confirmed that KD would lead to immune-mediated syndromes in certain genetically predisposed individuals.

KD is diagnosed clinically by identifying 5 out of 6 symptoms, including a fever lasting more than 5 days, conjunctiva injection, changes in the lips and oral mucosa, changes in the peripheral extremities, skin rash, and cervical lymphadenopathy (Morens DM. et al., National Surveillance of Kawasaki Disease. Pediatrics 65:21–25, 1980). Normally, the 5 out of the 6 symptoms are regarded as the criteria for determining KD.

Because of the varying severity and inconstant appearance of clinical manifestations, some patients with KD in whom characteristic coronary artery abnormalities developed after the onset of the illness that did not meet the criteria for determining KD, are diagnosed with what is called Atypical Kawasaki Disease (Rowley et al., Incomplete Kawasaki Disease with Coronary Artery Involvement. Eur J. Pediatr, 151:577–580, 1992). The diagnosis of AKD is difficult since those patients only have three or four out of six symptoms. Actually, to meet all of the criteria for determining KD is too strict to find AKD, which often results in sequels of myocardial infarction of sudden death. ALL patients with coronary artery vasculitis have less than four of the symptoms (Boven et al., Atypical Kawasaki Disease Citation: An Often Missed Diagnosis; (Joffe et al., Atypical and Complicated Kawasaki Disease in Infants, Do We Need Criteria?, West J. Med, 162:322–327, 1995). Coronary Artery Abnormality (CAA hereafter) is the most distinctive and fearsome complication accompanying KD, since it may cause sudden death from cardiac disease during the convalescent stage (Syed et al., Coronary Artery Aneurysm: A Review, Progress in Cardiovascular Diseases, 40:77–84, 1977). Early therapy with intravenous immunoglobulin (IVIG), sometimes combined with aspirin, was found to be effective in reducing the incidence of CAA in the acute phase (Furusho et al., Japanese Gamma Globulin Trials for Kawasaki Disease. In Shulman ST, ed. Kawasaki Disease. New York: AIan R. Liss Inc. pp. 425–432, 1986; Newburger et al., The Treatment of Kawasaki Syndrome With Intravenous Gamma Globulin. N Eng J Med 315:341–347, 1986).

A method of confirming the diagnosis of KD in patients by using anti-tumor necrosis factor monoclonal antibody was disclosed in U.S. Pat. No. 5,075,236. Further, U.S. Pat. No. 5,286,623 provided a method for screening for the possibility of KD in a patient which comprises assaying a T cell receptor containing a sample taken from said patient to determine the level of Vb2 or Vb8.1 by immunoassay or by measuring Vb2 or Vb8.1 mRNA. A method for screening for the possibility of KD in patients by using an antibody which specifically binds to toxic shock syndrome toxin-1 (TSST-1) was disclosed in U.S. Pat. No. 5,470,716. However, none of the above-mentioned references provides a precise diagnosis or detection of KD since the substances to be detected in those known methods would also be present in patients suffering from other diseases.

Given the above, there is an urgent and extremely important need to find an effective and specific method for diagnosis of KD and AKD at early stages so that a strategy for the treatment of KD or AKD can be decided earlier.

SUMMARY OF THE INVENTION

One objective of the invention is to provide a method for diagnosing Kawasaki disease (KD) in a patient suspicious of KD by using as an index a ratio of the blood level of haptoglobin (Hp) to the blood level of apolipoprotein AI (AI) in said patient.

In particular, the claimed invention provides a method for diagnosing Kawasaki disease (KD) in a patient suspicious of KD comprising:

(a) measuring the blood level (w/v) of haptoglobin (Hp) in said patient to obtain a value A;

(b) measuring the blood level (w/v) of apolipoprotein AI (Apo AI) in said patient to obtain a value B;

(c) calculating the ratio of A/B as an index;

(d) comparing the index A/B obtained in step (c) with an cut off value wherein based on the cut off value, the predictive value of a positive test (PPV) is higher than 70%; and (e) diagnosing said patient as suffering from KD if the index is higher than the cut off value.

Another objective of the invention is to provide a method for diagnosing atypical or typical Kawasaki disease in a patient suspicious of KD to determine the strategy of the treatment of KD earlier by using the phenotype of haptoglobin.

The invention also provides a system for diagnosing KD and/or AKD in a patient suspicious of KD.

DETAILED DESCRIPTION OF THE INVENTION

Figure 1:
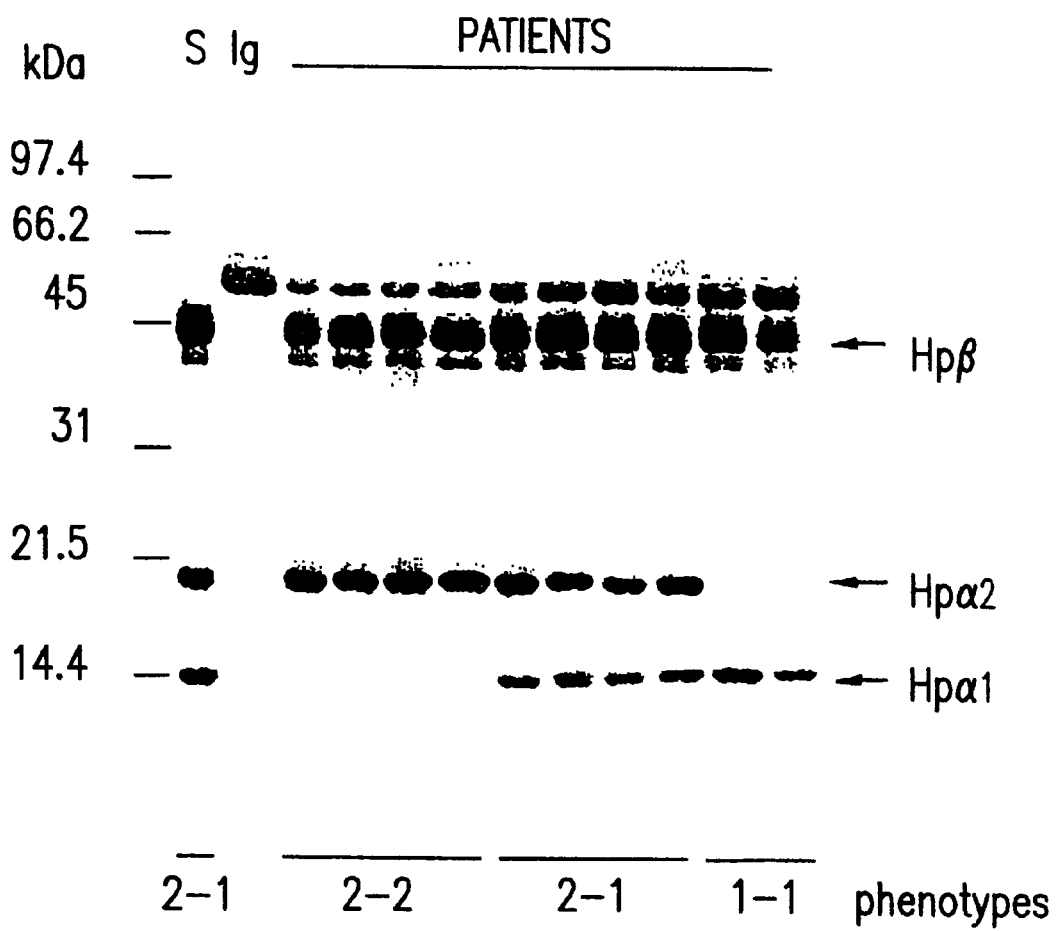
FIG. 1 shows the phenotypes of haptoglobin of the KD patients.

In one aspect, the present invention provides a method for the diagnosis of Kawasaki disease (KD) in a patient suspicious of KD by using as an index a ratio of a blood level (by weight/volume) of haptoglobin to a blood level (in weight/volume) of apolipoprotein AI (Apo AI, also referred to interchangeably herein as Apo AI) in said patient.

Haptoglobin (Hp) is a hemoglobin-binding acute phase protein which is present in most body fluids of humans and other mammals, such as blood. The blood level of Hp in a subject will increase when the subject suffers from inflammation, infections of different etiology, trauma, tissue damage and malignant proliferation, but will decrease when the subject is in hemolytic conditions and in severe hepatocellular deficiency. Thus, the change in the blood level of Hp can be used for the diagnosis and/or evaluation of the effect of a treatment of a patient under various pathological conditions (Dobryszycka W. 1997, Biological Functions of Haptoglobin-New Pieces to an Old Puzzle, Eurj Clin Chem Clin Biochem; 35:647–654).

The level of Hp can be measured by a nephelometric assay. The assay is sensitive and exhibits within-run precision in the range of 2.5–7.4% coefficient of variation (CV) and between-run precision of 7.0 (CV) (Lente et. al., Evaluation of a Nephelometric Assay for Haptoglobin and its Clinical Useness).

Apolipoprotein AI (Apo AI) is a major protein in blood which contain high density cholesterol at an amount of higher than 95%. The Apo AI can also be measured by a nephelometric assay.

In comparison with the patients suffering from other diseases, it is surprisingly found that the patients suffering from KD have significantly increased levels of Hp and significantly decreased level of Apo AI. Therefore, it is concluded in the present invention that the ratio of the blood level of Hp to the blood level of Apo AI (Hp/Apo AI) can be used as an index. According to the present invention, the method for diagnosing KD using the ratio has a high specificity.

In particular, the method for the diagnosis of Kawasaki disease (KD) in a patient suspicious of KD comprises:

(a) measuring the blood level (w/v) of haptoglobin (Hp) in said patient to obtain a value A;

(b) measuring the blood level (w/v) of apolipoprotein AI (Apo AI) in said patient to obtain a value B;

(c) calculating the ratio of A/B as an index;

(d) comparing the index A/B obtained in step (c) with an cut off value wherein based on the cut-off value, the positive predictive value (PPV) is higher than 70%; and (e) diagnosing said patient as suffering from KD if the index is higher than the cut-off value.

To ensure the accuracy of the diagnostic test, the specificity, sensitivity of the method of the invention and to the positive predictive value (PPV) is evaluated through the gold standard method (Charron et. al., Diagnostic Value of Electrocardiography and Echocardiography for Familial Hypertrophic Cardiomyopathy in a Genotyped Adult Population, Circulation Vol. 96, No. 1, pp.214–219, 1997), which is incorporated by reference.

According to the invention,he cut-off value can be determined by calculating the positive predictive value (PPV). The PPV is the predictive value of a positive test in a patient. For instance, when the PPV of a test for a patient is higher than 70%, it means that the possibility f the patient suffering from KD is higher than 70%. As shown in Table 2 in Example 1, it is found that when the cut-off value is 2.0, the PPV is higher than 70%. According to the present invention, the cut-off value can be 2.0 (the PPV is higher than 70%), preferably 3.0 (the PPV is higher than 90%), and most preferably 3.5 (the PPV is higher than 95%).

According to the invention, KD can be diagnosed earlier, such as in 3–10 days for a patient in the acute stage, preferable in 5–7 days and theoretically at first day of illness. The invention provides a simple, easy, economical and sensitive method for diagnosing KD.

According to the method of the invention, the level of Hp and the levels of Apo AI can be measured in any body fluid samples, preferably a blood sample. Preferably, the levels of the Hp and Apo AI in the samples be represented by weight/volume (w/v). The diagnosis of KD can be done by measuring the levels of Hp and Apo AI in a patient suspicious of KD, calculating the ratio (Hp/Apo AI) as an index, and comparing the ratio with the cut-off value to diagnose the patient as suffering from KD if the ratio is higher than the cut-off value.

In another aspect, the invention provides a method for diagnosing atypical or typical Kawasaki disease (KD) in a patient suspicious of KD to determine the strategy. of the treatment of KD earlier by using the phenotype of haptoglobin (Hp). The method comprises identifying the phenotype of haptoglobin (Hp) in the patient, determining the strategy of the treatment of KD earlier based on the phenotype of haptoglobin (Hp) identified in the above step.

Haptoglobin (Hp) displays genetic polymorphism. Three major phenotypes designated as Hp 1-1, Hp 2-1 and Hp 2-2 are two alleles $Hp^1$ and $Hp^2$. Hp polymorphism appears to be related to immune response and to autoimmune and inflammatory disorders (Angloisl et. el., 1996, Biological and Clinical Significance of Haptoglobin Polymorphism in Humans). The biological and clinical consequences of haptoglobin include inter alia the reaction of haptoglobin with haemoglobin, the antioxidant activity towards haemoglobin-stimulated lipid peroxidation and the inhibitory effect on prostaglandin synthesis (Dobryszycka W., Biologicsl Functions of Haptoglobin-New Pieces to an Old Puzzle, Eur J Clin Chem Clin Biochem 1997; 35: 647–654). However, none of the prior art discloses the relationship between haptoglobin and KD.

Normally, patients present atypical KD only-after 7 or more days following the onset of the disease. Therefore, many patients suffer from a delayed diagnosis and as a result are denied the benefits of early treatment. It is surprisingly found in the invention that the phenotypes of Hp were associated with CAA formation in KD. That is, it is found that most of the patients with Hp 2-2 were clinically diagnosed as typical KD, and most of the patients with Hp 2-1 and HP 1-1 were clinically diagnosed as atypical KD. If in a patient suspicious of KD), the phenotype of Hp is Hp 2-1 or Hp 1-1, it is suggested that the treatment of KD in the patient be determined within 7 days after the first day of illness to prevent the formation of CAA.

The present invention discloses that the levels of Hp in the acute stage vary based on the phenotypes of Hp. Based upon the identification of the phenotypes of Hp, the pediatricians may decide the strategy of the treatment of KD earlier, such as an IVIG therapy, or evaluate the timing for the treatment of KD, to prevent CAA. As shown in the invention, the cases suffering from CAA in the patients with Hp allele could be decreased from 48.1% to 8.3% if the patient was diagnosed as AKD and the treatment of KD was determined earlier.

In one embodiment, the present invention provides a system for diagnosing KD and/or AKD in a patient suspicious of KD. The system of the invention comprises:

(a) a means for measuring the level (w/v) of haptoglobin (Hp) in said patient to obtain a value A;

(b) a means for measuring the level (w/v) of apolipoprotein AI (Apo AI) in said patient to obtain a value B;

(c) a means for calculating the ratio of A/B as an index, and then comparing the index A/B with an cut off value wherein based on the cut-off value, the positive predictive value (PPV) is higher than 70%, to diagnose said patient as suffering from KD if the index (A/B) is higher than the cut-off value.

According to the invention, the means for detecting (including identifying and/or measuring the levels of) Hp and Apo AI respectively, include such as, a binding assay using the ligands specific to Hp, or Apo AI respectively. More preferably, the ligand may be a polyclonal antibody, most preferably monoclonal antibody. The polyclonal antibodies and/or monoclonal antibodies specific to the Hp or Apo AI can be prepared by standard techniques known in the art. The process for preparing the monoclonal antibody comprises preparing immortal cell line capable of producing antibodies having the desired specificity (reactivity with the Hp and Apo AI) through any fusion techniques, and obtaining hybridomas having high reactivity and specificity, and isolating the monoclonal antibodies from the supernatants of the hybridoma colonies. The polyclonal antibody can be commercial available (such as Calbiochem Inc., USA).

Any known or conventional methods for detecting Hp or Apo AI can be used in the invention. In a preferred embodiment, the levels of Hp or Apo AI can be measured by an assay using antibodies immobilized on a solid support. The bound Hp or Apo AI may then be detected using a detection reagent that contains a reporter. Suitable detection reagents include any compound that binds to the immobilized antibody-Hp/Apo AI complex and that can be detected. Preferred reporters include enzymes, substrates, cofactors, inhibitors, dyes, radioactive substances, luminescent substances and fluorescent substances. The conjugation of a binding agent to a reporter may be achieved using standard methods known in the art. Common binding agents may also be commercial available.

The detection reagent is then incubated with the immobilized antibody-Hp/Apo AI complex for a time sufficient to detect the bound Hp/Apo AI. Unbound detection reagent is then removed and bound detection reagent is detected using the reporter group. The methods employed for detecting the reporters depend upon the natures of the reporters. For radioactive substances, scintillation counting or autoradiographic methods are generally appropriate. Spectroscopic methods may be used to detect dyes, luminescent groups and fluorescent groups. Enzymes as reporters may generally be detected by adding substrates, followed by spectroscopic or other analysis of the products.

The solid support may be any solid material known to those of ordinary skill in the art to which the antibodies may be attached. For example, the solid support may be a test well in a micrometer plate or a nitrocellulose or other suitable membrane. Alternatively, the support may be a bead or disc, such as glass, fiberglass, latex or a plastic material such as polystyrene or polyvinylchloride.

The antibodies may be bound to the solid support using a variety of techniques known to those skilled in the art. According to the invention, the term "bound" used herein refers to both noncovalent association (such as adsorption) and covalent linkage (which may be a direct linkage or a cross-linking agent).

In special embodiments, the assay is an enzyme linked immunosorbent assay (ELISA). The assay may be performed by first contacting an antibody that has been immobilized on a solid support with the sample, such that Hp and Apo AI within the sample are allowed to bind to the immobilized antibody. The unbound sample is removed from the immobilized antibody and a detection agent capable of binding to the immobilized antibody-Hp/Apo AI complex is added.

In another embodiment, the invention provides a system for diagnosing the AKD or KD in a patient suspicious of KD to determine the strategy of the treatment of KD earlier, comprising a means for identifying the phenotype of Hp in the patient wherein if the phenotype of Hp in the patient is Hp 2-1 or Hp1-1, it is suggested that the treatment of KD in the patient be determined within 7 days after the first day of illness to prevent the formation of CAA. The means for identifying the phenotype of Hp includes such as a binding assay using the ligands specific to Hp a2 subunit and Hp a1 subunits for identifying the phenotypes Hp 1-1, Hp 1-2 and Hp2-2. The phenotypes of haptoglobin can also be determined by using the methods known in the art such as sodium dodecyl-sulfate (SDS) gel electrophoresis or isoelectric focusing in poltacrylamide gels followed by immunoblotting as described above using specific antibody to Hpa1 pr Hpa2 subunits.

The following Examples are offered by way of illustration and not by way of limitation.

EXAMPLES

Example 1

The Diagnosis of KD by Using a Ratio of Hp/Apo AI

Sample Collection

The diagnosis of KD was based on clinical criteria established by the Center for Disease Control (CDC, Morens et al., 1980) (Morens et al., Pediatrics 65:21, 1980) by the physicians from Department of Pediatrics of Kaohsiung Medical College, Taiwan. The serum samples were collected from the KD patients. The samples from the patient without KD admitted to outpatient clinics were consecutively collected as normal controls. In addition, the serum samples from pneumonia patients having a prolonged fever but without KD were consecutively collected as illness controls to clarify the specificity of the method of the invention. All the serum samples were stored at 4° C. within 24 hours or at 20° C. for 1 month before the samples were biochemically characterized.

Determination of Hp and Apo AI by Immunone

The frozen or fresh sera samples were warmed back to room temperature. Levels of Hp and Apo AI were measured by rate immunonephelomety (INTMGE™ immunochemistry Systems, Beckman, USA).

Results

The changes of the blood levels of Hp and Apo AI in KD patients, pneumonia patients and normal patients are shown in Table 1. The blood levels of Hp in KD children were about 5.6 times greater than that in the normal children. However, the levels of Apo AI in KD children were about 52% less than those of normal children. The levels of Hp in children with pneumonia only were about 3.0 times greater than those of the normal children. The levels of Apo AI in children with pneumonia were 35% less than those of the normal children.

The ratios (Hp/ Apo AI) in KD patients and normal patients were significantly different. The ratios in KD patients were respectively 13.6 times and 2.45 times greater than those of normal children and children with pneumonia (Table 1). Therefore, it was suggested that the ratio (Hp/Apo AI) could be used as an index to diagnose KD. The sensitivity, specificity and the positive predictive value for different cut-off values were given in Table 2. The sensitivity is calculated by the formula:

true-positive/(true-positives+false-negatives)×100.

The specificity was calculated by the formula:

true-negatives/(true-negatives+false-negative)×100.

The PPV was calculated by the formula:

true-negatives/(true-positives+false-positives)×100.

As shown in Table 2, it could be concluded that the cut-off values are higher than 2.0 showing that the PPV is higher than 70%, the satisfactory sensitivity and specificity could be obtained for the patients having either prolonged fever for 5–10 days, or fever for 5–7 days.

days with clinical findings and complications was defined as in "subacute" stage of KD. For comparison of distribution of Hp phenotypes between patients with KD and the referenced population, the serum samples from children admitted to outpatient clinics were consecutively collected.

Methods

The serum samples were separated from freshly drawn blood and then divided into aliquots stored at −20° C. for clinical chemical tests and laboratory tests. The levels of Hp

TABLE 1

Clinical and laboratory data of controls and patients with Kawasaki disease

| Clinical and laboratory data | Controls Healthy | Controls Pneumonia | Kawasaki disease |
|---|---|---|---|
| Sex. M/F | 23/12 (35) | 15/5 (20) | 20/13 (33) |
| Age, month | 29.63 ± 14.62[a] (35) | 27.20 ± 18.34[a] (20) | 18.79 ± 13.96[b] (33) |
| Days after onset of fever | — | 6.80 ± 1.58[a] (20) | 6.64 ± 1.37[a] (33) |
| Platelet, × 1000/mm$^3$ | 315.59 ± 116.82[a] (17) | 298.08 ± 137.74[a] (13) | 350.75 ± 156.86[a] (28) |
| WBC, × 1000/mm$^3$ | 9.56 ± 3.24[b] (16) | 8.99 ± 2.98[b] (14) | 13.88 ± 5.81[a] (28) |
| CRP, mg/mL | — | 18.99 ± 50.50[b] (14) | 87.67 ± 77.19[a] (23) |
| Hp, mg/dL | 59.42 ± 42.91[c] (33) | 197.45 ± 94.94[b] (17) | 332.58 ± 94.45[a] (33) |
| Apo AI, mg/dL | 188.53 ± 34.72[a] (34) | 122.44 ± 28.38[b] (17) | 89.91 ± 34.78[c] (33) |
| Apo B, mg/dL | 74.14 ± 19.99[b] (34) | 82.19 ± 31.10[ab] (17) | 88.68 ± 24.11[a] (33) |
| Hp/Apo AI | 0.315 ± 0.143[c] (33) | 1.753 ± 1.010[b] (17) | 4.309 ± 2.17[a] (33) |

Abbreviations: Apo AI, apolipoprotein AI; Apo B, apolipoprotein B; CRP, C-reactive protein; F, female; Hp, haptoglobulin; Hp/Apo A-I, ratio of Hp to Apo AI; M, male; WBC, white blood cell. Values are mean ± standard deviation (SD) and number of cases studied are presented in parenthesis. The superscript with different letters in the same row are significantly different (P < 0.05).

TABLE 2

Sensitivity, specificity, positive predictive value, and negative predictive value for Hp/Apo A1 to diagnose KD

| Hp/Apo A1 Cut-off value | Sensitivity | Specificity | PPV* |
|---|---|---|---|
| Prolonged fever for 5–10 days before final diagnosis of KD | | | |
| 3.5 | 0.697 | 0.941 | 0.958 |
| 3.0 | 0.758 | 0.882 | 0.926 |
| 2.5 | 0.788 | 0.706 | 0.839 |
| 2.0 | 0.879 | 0.412 | 0.744 |
| Prolonged fever for 5–7 days before final diagnosis of KD | | | |
| 3.5 | 0.615 | 0.933 | 0.941 |
| 3.0 | 0.731 | 0.867 | 0.905 |
| 2.5 | 0.769 | 0.667 | 0,800 |
| 2.0 | 0.885 | 0.600 | 0.793 |

*PPV: positive predictive value

Example 2

The Diagnosis of AKD by Using the Phenotype of Hp

Sample Collection

The subjects to be tested are 54 children with KD aged from 3 months to 5 years and 10 months (shown in Table 3), who were the patients consecutively admitted to the Department of Pediatrics, Chung-Ho Memorial Hospital, Kaohsiung Medical College, Taiwan. The patients were hospitalized for the days of an average of 8.5 days, a range of 2–28 days. The diagnosis of KD was based on the clinical criteria established by the Center for Disease Control (CDC, Morens et al., 1980). The definition of disease stages was followed the classification of Schaller (1996), which was modified from Hicks and Melish (1986). Accordingly, a duration of 1–10 days with major clinical findings and complications was defined as in "lacute" stage of KD. Duration of 11–21 days with clinical findings and complications was defined as in "subacute" stage of KD. For comparison of distribution of Hp phenotypes between patients with KD and the referenced population, the serum samples from children admitted to outpatient clinics were consecutively collected.

were measured by rate immunonephelometry (IMMAGE™ immunochemistry Systems, Beckman, USA). A two-dimensional echocardiography was done for all patients with typical or atypical KD. The echocardiographic criteria for evaluating the CAA, including dilatation and aneurysm, were adopted from those of the KD Research Committee in Japan. The criteria consisted of an increase in coronary artery diameter of 3.0 mm or greater. In Table 3, with the exception of 7 patients who were diagnosed as having KD in subacute stage and were not subjected to WVIG treatment, all of the remaining 47 KD patients (41 diagnosed in acute stage and 6 in subacute stage) were administered with a high dose of WVIG (2 g/kg body weight) plus aspirin (60–80 mg/kg body weight). During recovery from subacute KD, all the patients were prescribed a low dose of aspirin (3–5 mg/kg body weight). 22

The levels of serum proteins were determined by the Lowry method. The samples of 100 mg serum protein for Western immunoblotting were first resolved by 12.5% sodium dodecylsulfate polyacrylamide gel electrophoresis (SDS-PAGE). After electrophoresis, the gel was soaked in a transfer buffer (50 mM Tris-borate, pH8.3, 1 mM EDTA) for 10 min. Resolved proteins were then electro-transferred onto a nitrocellulose membrane by a semi-dry method (OWL Scientific Plastics Inc.: Cambridge, MA). The membrane was incubated for 1 hr with 3% gelatin in Tween containing Tris buffered saline (TTBS: 20 mM Tris-HCl, pH 7.4, 500 mM NaCl, 0.05% Tween 20) and then rinsed with TRBS. Subsequently, the membrane was incubated with polyclonal antibody to human Hp (Calibiochem; diluted 1:5000 in TTBS containing 1% gelatin) at room temperature for 30 minutes. After washed three times with TTBS, the membranes were reacted with goat anti-rabbit antibody conjugated with alkaline phosphatase (Sigma: diluted 1:5000 in TTBS containing 1% gelatin) at room temperature for 30 minutes. The membrane was then rinsed three times with TTBS and developed at room temperature in a developing buffer (15 mg of nitro blue tetrazolium, 0.7% N,N-dimethylformamide, 30 mg of 5-bromo-4-chloro-3-indolyl phosphate per 100 ml, 1 mM MgCl$_2$, and 100 mM NaHCO$_3$, pH9.8).

Results

The Hp phenotype in the patients with KD (FIG. 1 and Table 3) was determined and the distribution of Hp phenotypes with the referenced controls was compared.

As the results shown in Table 3, by $X^2$ statistical analysis, the distribution of the three major phenotypes Hp 2-2, Hp 2-1 and Hp 1-1 in the KD group were not significantly different from that of the referenced group as denoted Taiwan 1998.

TABLE 3

Distribution of haptoglobin phenotypes in patients with Kawasaki disease and referenced populations

| Populations | Distribution of haptoglobin phenotypes (% of population) | | | | Frequency of Hp[1] |
|---|---|---|---|---|---|
| | Hp 2-2 | Hp 2-1 | Hp 1-1 | Hp 0-0 | |
| Kawasaki disease[#] | 50.0 | 42.6 | 7.4 | 0.0 | 0.293 |
| (n = 54) | (27) | (23) | (4) | (0) | |
| Referenced | | | | | |
| Taiwan 1998 | 55.1 | 34.3 | 9.6 | 1.01 | 0.258 |
| (Kaohsiung)[#] | | | | | |
| (n = 198) | (109) | (68) | (19) | (2) | |
| Taiwan 1962 (Taipei) | 52.9 | 37.7 | 9.3 | 0.0 | 0.273 |
| China 1983 (Han) | 53.7 | 37.1 | 8.2 | 0.89 | 0.267 |

References: Taiwan 1998, Lee et al., 1998; Taiwan 1962, Blackwell et al., 1962; China 1983, Lianh et al., 1983.
[#]The distribution of haptoglobin between patients with Kawasaki disease and the referenced population in Taiwan are not significantly different ($P > 0.05$).

Figure 2A:
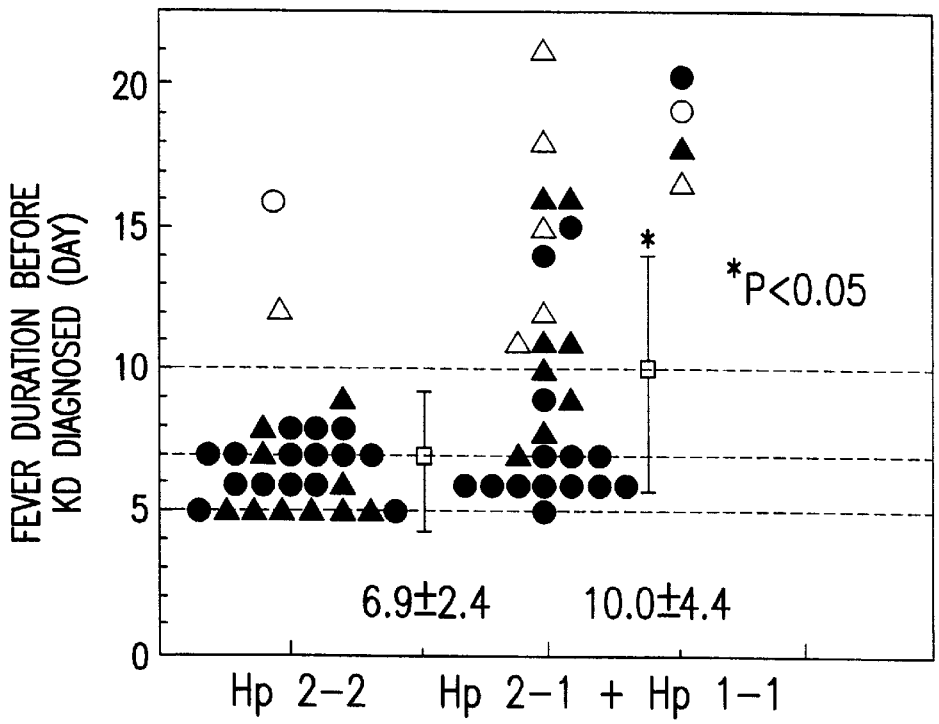
FIG. 2(a) shows the days for which the patients suspicious of KD had a fever, and the phenotypes of Hp present in the patients.
Figure 2B:
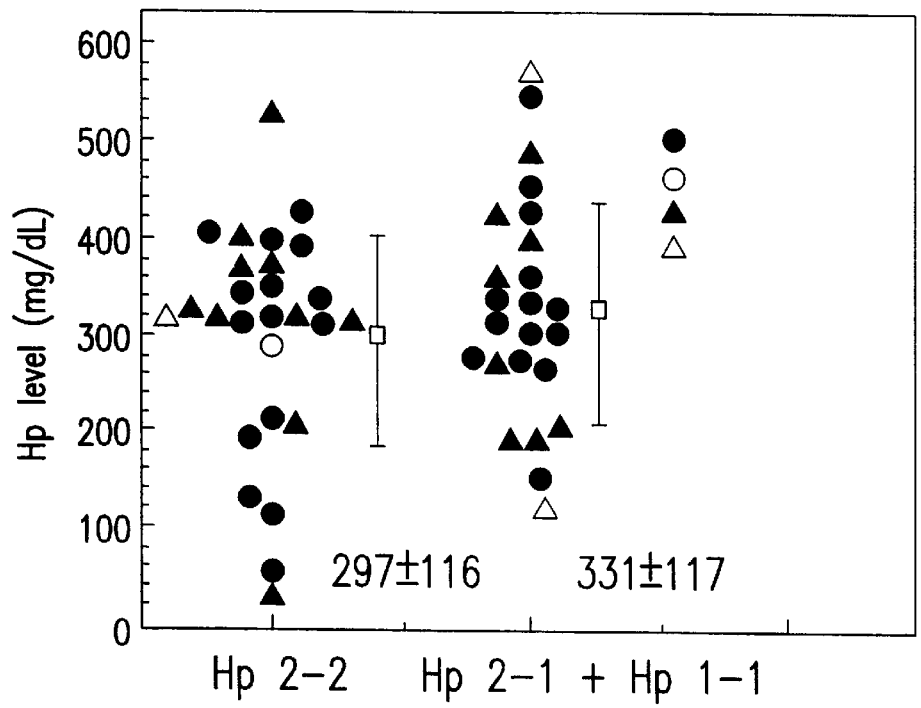
FIG. 2(b) shows the Hp levels in the patients with Hp phenotype, Hp 2-2 and Hp 2-1 plus Hp 1-1.

It was suggested that Hp phenotype was related to the formation of CAA. As shown in Table 4, the KD patients with phenotype Hp 2-2 were diagnosed in an acute stage and then these patients had CAA. In contrast, of the KD patients with phenotype Hp 2-1 who were diagnosed in an acute stage and then the patients had CAA. The patients with Hp phenotype 2-1 were diagnosed lately in subacute stage and then the patient had CAA. More surprisingly, all of the KD patients with Hp 1-1 were diagnosed as having CAA in a subacute stage. The percentage of CAA formation in the KD patients with three Hp phenotypes were different in which the patients with Hp allele 1 had a higher incidence of developing CAA. FIG. 2 demonstrated that a duration of fever before KD diagnosed was different in Hp phenotype (6.90±2.4 days vs. 10.0±4.4 days in Hp 2-2 vs. Hp 2-1 plus Hp 1-1, P=0.05). From the above results, it is indicated that serum Hp levels as well as its phenotypes are associated with the formation of CAA. However, the KD in the patients with HP[1] allelle cannot be diagnosed early and thus the appropriate treatment cannot be determined earlier. Therefore, it is suggested that the patients suspicious of KD with HP[1] allelle be treated with IVIG within 7 days to prevent the formation of CAA.

TABLE 4

Association between formation of coronary artery abnormalities and haptoglobin phenotypes in patients with KD during stages

| | | Formation of coronary artery abnormality (%) | | | |
|---|---|---|---|---|---|
| | Disease | Disease stage divided by 10th day | | Hypothetical timing for IVIG treatment | |
| Haptoglobin phenotype | stage not divided | Acute (10 d) | Subacute (>10 d) | Timing 1 (7 d) | Timing 2 (> 7 d) |
| Overall | 44.4 | 35.7 | 75.0 | 28.1 | 72.7 |
| | (24/54) | (15/42)* | (9/12)* | (9/32)* | (16/22)* |
| Hp 2-2 | 40.7 | 40.0 | 50.0 | 40.0 | 42.9 |
| | (11/27)[@] | (10/25)[@] | (1/2)[@] | (8/20)≠ | (3/7)[@] |
| Hp[1] allele | 48.1 | 29.4 | 80.0 | 8.3 | 80.0 |
| | (13/27)[@] | (5/17)*[@] | (8/10)*[@] | (1/12)*≠ | (12/15)*[@] |
| Hp 2-1 | 47.8 | 31.3 | 85.7 | 9.1 | 83.3 |
| | (11/23) | (5/16) | (6/7) | (1/11) | (10/12) |
| Hp 1-1 | 50.0 | 0.0 | 66.7 | 0.0 | 66.7 |
| | (2/4) | (0/1) | (2/3) | (0/1) | (2/3) |

Abbreviations: Hp, haptoglobin; IVIG, intravenous immunoglobulin; KD, Kawasaki disease.
[@]The association between CAA formation and Hp phenotypes are not significant difference ($P > 0.05$) when KD disease stage was not divided by the 10th day.
*The association between CAA formation and fever days by stage before KD diagnosed differs significantly ($P < 0.05$).
≠The association between CAA formation and Hp phenotypes are significant difference ($p < 0.05$) when the hypothetical effective timing for IVIG treatment was set within 7 days.

What is claimed is:

1. A method for diagnosing Kawasaki disease (KD) in a patient suspected of suffering from KD comprising:
   (a) measuring the blood level (w/v) of haptoglobin (Hp) in said patient to obtain a value A;
   (b) measuring the blood level (w/v) of apolipoprotein A1 (Apo A1) in said patient to obtain a value B;
   (c) calculating the ratio of A/B as an index;
   (d) comparing the index A/B obtained in step (c) with a cut off value wherein based on the cut off value, the predictive value of a positive test (PPV) is higher than 70%; and
   (e) diagnosing said patient as suffering from KD if the index is higher than the cutoff value.

2. A method according to claim 1, wherein the cut off value is 2.0.

3. A method according to claim 1, wherein the cut off value is 3.0.

4. A method according to claim 1, wherein the cut off value is 3.5.

5. The method according to claim 1, wherein the KD is diagnosed within 3–10 days.

6. The method according to claim 5, wherein the KD is diagnosed within 5–7 days.

7. The method of claim 1, wherein said value A is determined by performing an immunoassay comprising a ligand specific to Hp.

8. The method of claim 1, wherein said value B is determined by performing an immunoassay comprising a ligand specific to Apo AI.

9. A method for diagnosing atypical Kawasaki disease (AKD) in a patient to determine a strategy of treatment comprising:
   (a) identifying the phenotype of haptoglobin (Hp) in said patient, and
   (b) correlating the presence of Hp2-1 or Hp 1-1 haptoglobin phenotype with AKD thereby diagnosing AKD; and providing treatment to the patient.

10. The method according to claim 9 wherein the treatment of the patient for KD is within seven days following the first day of illness.

* * * * *

UNITED STATES PATENT AND TRADEMARK OFFICE
CERTIFICATE OF CORRECTION

PATENT NO. : 6,451,542 B1
DATED : September 17, 2002
INVENTOR(S) : Lee et al.

It is certified that error appears in the above-identified patent and that said Letters Patent is hereby corrected as shown below:

Column 1,
Line 6, change "to t" to -- to the detection --;
Line 7, change "a typical" to -- atypical --,
Column 3,
Between lines 4 and 5, please insert the paragraph:
    -- It is suprisingly found in the present invention that the ratio of the blood level (by weight/volume, w/v) of haptoglobin (Hp) to the blood level (by weight/volume, w/v) of apolipoprotein AI (Apo A1) can be used as an index to diagnose KD. --;

Column 7,
Line 67, change "lacute" to -- acute --,

Column 8,
Line 39, change "WVIG" to -- IVIG --;
Line 42, change "WVIG" to -- IVIG --;
Line 55, change "TRBS" to -- TTBS --;

Column 10,
Line 61, change "AKD" to -- AKD, --;

Signed and Sealed this

Twenty-first Day of January, 2003

JAMES E. ROGAN
*Director of the United States Patent and Trademark Office*